(12) United States Patent
Mukaide

(10) Patent No.: US 10,088,437 B2
(45) Date of Patent: Oct. 2, 2018

(54) COMPUTING DEVICE, COMPUTING PROGRAM, X-RAY MEASURING SYSTEM AND X-RAY MEASURING METHOD

(71) Applicant: CANON KABUSHIKI KAISHA, Tokyo (JP)

(72) Inventor: Taihei Mukaide, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 54 days.

(21) Appl. No.: 14/441,494

(22) PCT Filed: Oct. 28, 2013

(86) PCT No.: PCT/JP2013/079659
§ 371 (c)(1),
(2) Date: May 7, 2015

(87) PCT Pub. No.: WO2014/073462
PCT Pub. Date: May 15, 2014

(65) Prior Publication Data
US 2015/0293041 A1  Oct. 15, 2015

(30) Foreign Application Priority Data
Nov. 12, 2012  (JP) .................. 2012-248625

(51) Int. Cl.
| G01N 23/083 | (2006.01) |
| G01N 23/207 | (2018.01) |
| G01N 23/046 | (2018.01) |

(52) U.S. Cl.
CPC ......... *G01N 23/083* (2013.01); *G01N 23/046* (2013.01); *G01N 23/207* (2013.01);
(Continued)

(58) Field of Classification Search
CPC combination set(s) only.
See application file for complete search history.

(56) References Cited

U.S. PATENT DOCUMENTS

2007/0183563 A1\* 8/2007 Baumann ............... A61B 6/032
378/19

FOREIGN PATENT DOCUMENTS

| DE | 10 2006 037255 A | 8/2007 |
| JP | 3864262 B2 | 12/2000 |

(Continued)

OTHER PUBLICATIONS

Zhihua Qi et al, "Quantitative imaging of electron density and effective atomic number using phase contrast CT", Physics in Medicine and Biology, Institute of Physics Publishing, Bristol GB, vol. 55, No. 9, May 7, 2010, p. 2669-2677.\*

(Continued)

*Primary Examiner* — Phillip A Johnston
*Assistant Examiner* — Hsien Tsai
(74) *Attorney, Agent, or Firm* — Canon USA Inc., IP Division

(57) ABSTRACT

A computing device configured to obtain information about a subject using a detection result detected by an X-ray detector which detects an X-ray passing through the subject, which device includes: a unit configured to obtain a detection result of the X-ray detector; a first obtaining unit configured to obtain a complex refractive index of the X-ray after passing through the subject using the detection result; and a second obtaining unit configured to obtain information about the subject in accordance with a correlation between the complex refractive index and a mass absorption coefficient.

24 Claims, 5 Drawing Sheets

(52) U.S. Cl.
CPC ........... *G01N 2223/3306* (2013.01); *G01N 2223/419* (2013.01); *G01N 2223/612* (2013.01)

(56) References Cited

FOREIGN PATENT DOCUMENTS

| JP | 2007-203065 A | 8/2007 |
|----|---------------|--------|
| JP | 4512660 B2    | 10/2009 |
| JP | 6168753 B2    | 7/2017 |

OTHER PUBLICATIONS

Qi, Z., et al., "Quantative imaging of electron density and effective atomic number using phase contrast CT", Phys. Med. Biol., Apr. 2010, pp. 2669-2677, vol. 55.

Donath, T., et al., "Towards Clinical X-Ray Phase-Contrast CT; Demonstration of Enhanced Soft-Tissue Contrast in Human Specimen", Invest. Radiol. 2010.

Kikuta, S., "X-ray scattering and synchrotron radiation science: fundamentals", Aug. 24, 2011, University of Tokyo Press.

\* cited by examiner

COMPUTING DEVICE, COMPUTING PROGRAM, X-RAY MEASURING SYSTEM AND X-RAY MEASURING METHOD

TECHNICAL FIELD

The present invention relates to a computing device used for X-ray measurement. The present invention relates also to peripheral technology of the computing device.

BACKGROUND ART

An X-ray is an electromagnetic wave having energy of about 10 eV or greater. Non-destructive testing using X-rays are employed widely in, for example, the industrial and medical fields.

For example, a method for quantitatively obtaining physical property values of a subject in accordance with absorption or phase shift of the X-ray after passing through the subject has been proposed.

PTL 1 discloses a method for obtaining information about electron density distribution and effective atomic number distribution of a subject on the basis of two or more X-ray absorption contrast images using a monochromatic X-ray having two or more energies (wavelengths).

PTL 2 discloses a method for obtaining distribution of an effective atomic number of a subject on the basis of information about absorption and phase shift of an X-ray after passing the subject.

CITATION LIST

Patent Literature

PTL 1 Japanese Patent No. 3864262
PTL 2 Japanese Patent No. 4512660

SUMMARY OF INVENTION

Technical Problem

The information obtained in PTL 1 and PTL 2 is only the electron density distribution and the effective atomic number. Only the electron density distribution and the effective atomic number may sometimes be insufficient as information when, for example, it is necessary to identify materials of a subject to measure.

Solution to Problem

The present invention provides a computing device configured to obtain information about a subject using a detection result detected by an X-ray detector which detects an X-ray passing through the subject, which device includes: a unit configured to obtain a detection result of the X-ray detector; a first obtaining unit configured to obtain a complex refractive index of the X-ray after passing through the subject using the detection result; and a second obtaining unit configured to obtain information about the subject in accordance with a correlation between the complex refractive index and a mass absorption coefficient.

Other aspects of the present invention will become apparent from the embodiments described below. Further features of the present invention will become apparent from the following description of exemplary embodiments with reference to the attached drawings.

DESCRIPTION OF EMBODIMENTS

A computing device according to an embodiment of the present invention obtains at least one piece of information (a physical property value) among a mass absorption coefficient, mass density, an average atomic number and an average mass number of a subject on the basis of a complex refractive index of an X-ray with respect to the subject in accordance with a correlation between the complex refractive index and the mass absorption coefficient. In this description, obtainment of a physical property value of a subject with reference to a previously created table is also called "obtainment." The method for obtaining the complex refractive index is not particularly limited.

Hereinafter, the computing device of the present embodiment will be described in more detail with reference to a correlation between a complex refractive index and a mass absorption coefficient, and with reference to a method for obtaining a mass absorption coefficient, mass density, an average atomic number and an average mass number in accordance with the correlation.

Figure 2:
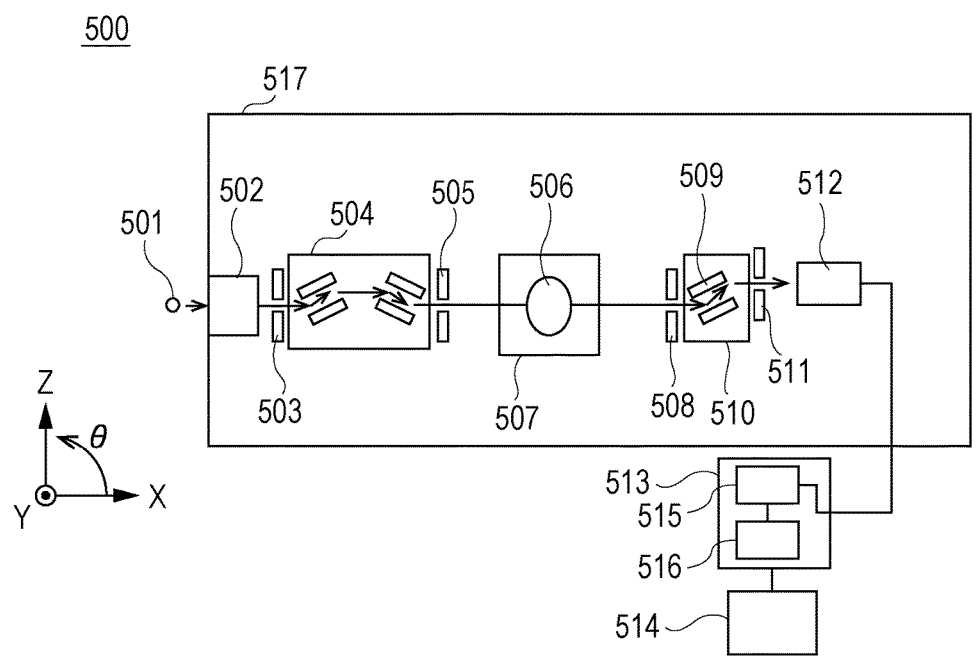
FIG. 2 is a schematic diagram of an X-ray measuring system according to an embodiment.

A computing device 513 according to the present embodiment includes a computing unit 515 and a storage unit 516. The computing device 513 is connected to an X-ray measuring device 517 to form an X-ray measuring system 500. An exemplary configuration of the X-ray measuring system 500 is illustrated in FIG. 2.

In the present embodiment, the computing unit 515 includes a unit for obtaining a detection result from an X-ray detector 512 which is provided in the X-ray measuring device 517. The detection result may be obtained directly or indirectly from the X-ray detector 512. Obtaining the detection result indirectly means that, for example, the storage unit 516 which will be described later obtains a detection result from the X-ray detector 512, and the unit for obtaining the detection result provided in the computing unit 515 obtains the detection result from the storage unit 516. The computing unit 515 includes a first obtaining unit which obtains a complex refractive index of the X-ray after passing through the subject 506 using the obtained detection result, and a second obtaining unit which obtains information about the subject 506 in accordance with a correlation between a complex refractive index and a mass absorption coefficient. The computing unit 515 may be configured by, for example, a CPU.

The storage unit 516 may store a measurement result of the X-ray measuring device 517 and physical property values of the subject 506 obtained by the computing unit 515. The storage unit 516 is configured by a nonvolatile storage medium. The storage unit 516 stores an operation program for the computing unit 515. The computing unit 515 obtains the physical property values of the subject 506 by performing computation in accordance with the program. Note that the storage unit 516 may store an operation program for an X-ray measurement to be performed by the X-ray measuring device 517 and the X-ray measuring device 517 may perform the X-ray measurement in accordance with the program. The operation program for the computing unit 515 may be stored in a storage media other than the storage unit 516. For example, the operation program may be stored on an external storage medium, such as a CD-ROM. The computing device 513 may load the operation program before the computing unit 515 executes the same.

Figure 1:
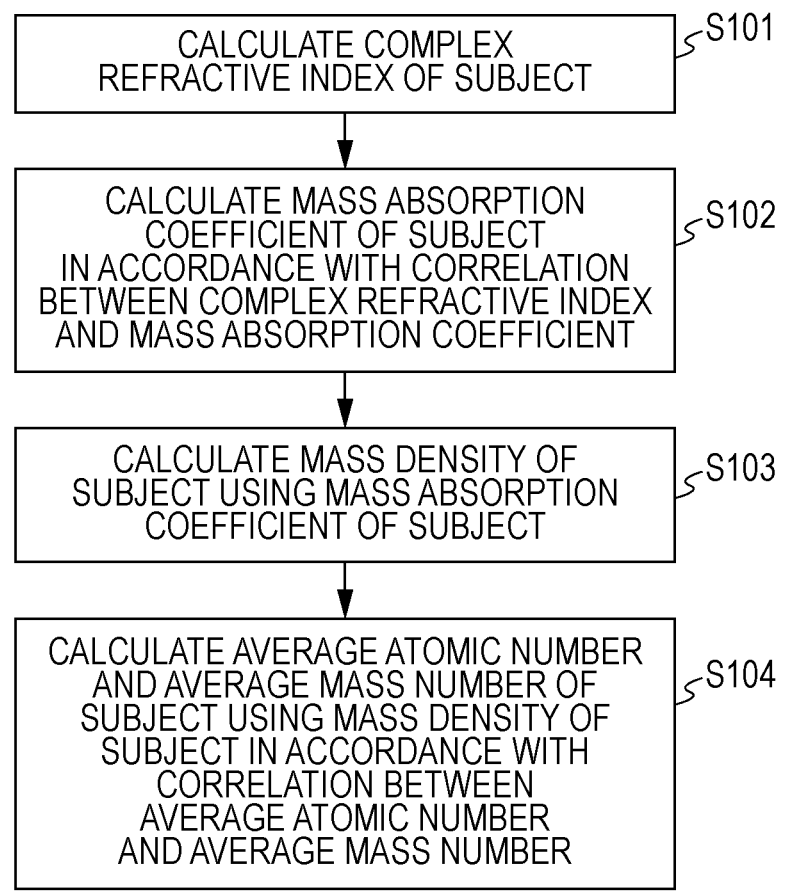
FIG. 1 is a diagram illustrating a computing flow of a computing device.

A computing flow performed by the first obtaining unit and the second obtaining unit of the computing unit 515 is illustrated in FIG. 1. First, the first obtaining unit obtains a complex refractive index of the subject 506 on the basis of the measurement result of the X-ray measuring device 517 (S101). Then the second obtaining unit obtains a mass absorption coefficient of the subject 506 using the complex refractive index obtained by the first obtaining unit in accordance with the correlation between the complex refractive index and the mass absorption coefficient (S102). Next, the second obtaining unit obtains mass density of the subject 506 using the mass absorption coefficient of the subject 506 obtained in S102 (S103). Next, the second obtaining unit obtains an average atomic number and an average mass number of the subject 506 using mass density of the subject 506 obtained in S103 in accordance with the correlation between the average atomic number and the average mass number (S104). Hereinafter, each step will be described.

First, a step of obtaining the complex refractive index of the subject 506 on the basis of the measurement result of the X-ray measuring device 517 (S101) will be described. The complex refractive index of the X-ray with respect to a material is expressed by Equation (1):

$$n = 1 - \delta - i\beta \quad (1)$$

in which $\delta$ in a real part in Equation (1) is a term related to a phase ($\Phi$) of the X-ray. A relationship between $\delta$ and the phase ($\Phi$) of the X-ray is defined by Equation (2):

[Math. 1]

$$\phi = \frac{2\pi}{\lambda} \int_0^t \delta \, dt \quad (2)$$

in which $\lambda$ is a wavelength of the X-ray and t is an optical path length of the X-ray within the material.

$\beta$ in an imaginary part in Equation (1) is a term related to absorption of the X-ray. Between the mass absorption coefficient ($\mu/\rho$) of the material with respect to the X-ray and $\beta$, there is a relationship expressed by Equation (3):

[Math. 2]

$$\left(\frac{\mu}{\rho}\right)\rho t = \frac{4\pi}{\lambda} \int_0^t \beta \, dt \quad (3)$$

in which $\rho$ is the mass density of the material.

Figure 3:
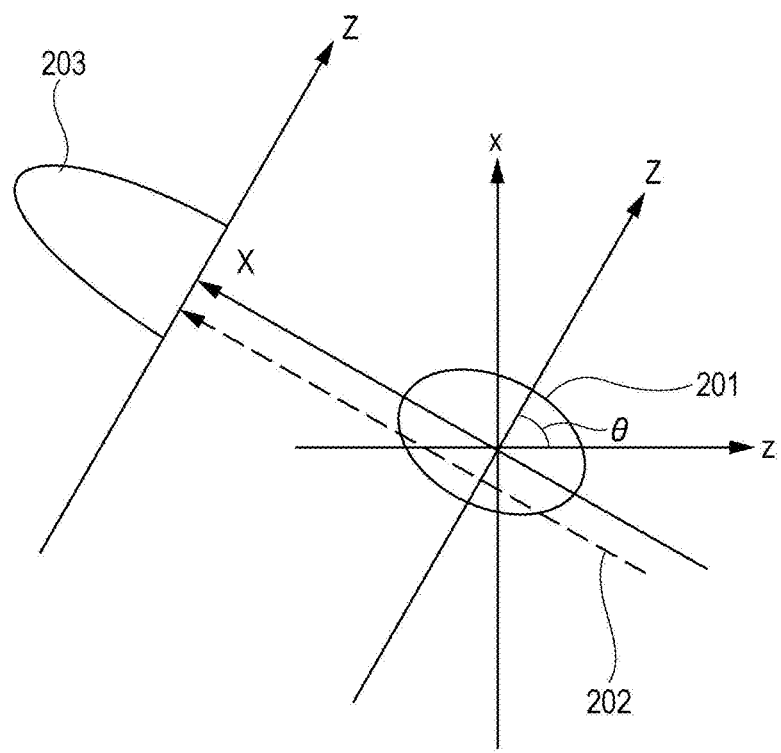
FIG. 3 is a schematic diagram illustrating a measurement using X-ray computed tomography.

Values of $\delta$ and $\beta$ may be computed if the chemical composition of the subject, the energy (i.e., a wavelength) of the X-ray, and the mass density are provided. If the chemical composition of the material is not provided, $\delta$ and $\beta$ may be obtained by using, for example, computed tomography (X-ray computed tomography). A principle of a measurement using the X-ray computed tomography is illustrated in FIG. 3.

Figure 4:
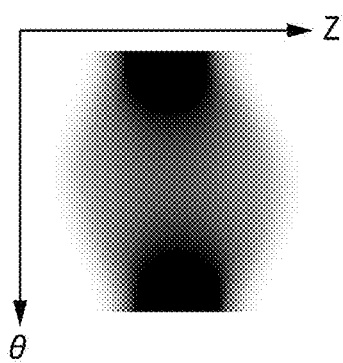
FIG. 4 is a diagram illustrating sinogram.

In the measurement using the X-ray computed tomography, intensity information, which is projection data 203, of the X-ray is obtained while changing an incidence angle $\theta$ of an X-ray 202 with respect to a subject 201. In FIG. 3, an x-axis and a z-axis represent coordinates with respect to the subject 201. The X-axis represents a direction in which the subject 201 is illuminated by the X-ray 202 and the Z-axis represents an axis perpendicular to the X-axis. A detector plane of the X-ray detector 512 is disposed in parallel with the Z-axis. FIG. 4 is an exemplary image called sinogram in which projection data 203 measured in a range in which $\theta$ is from 1 to 180 degrees is plotted with the horizontal axis representing Z and the vertical axis representing $\theta$. It is possible to obtain information about a tomographic image of the subject 201 from the projection data 203 using a reconstruction algorithm.

When the X-ray 202 passes through the subject 201, the X-ray 202 is absorbed by the subject 201; therefore, the intensity of the X-ray 202 is reduced and the phase of the X-ray 202 is shifted. If the projection data 203 is on the basis of the product of a linear absorption coefficient ($\mu$) obtained from the transmittance of the X-ray 202 and the optical path length (t) of the X-ray 202 within the subject 201, the information about the tomographic image regarding the value of $\beta$ with respect to the subject 201 may be obtained by reconstruction.

If the projection data is related to a phase shift of the X-ray, the information about the tomographic image regarding the value of $\delta$ may be obtained by reconstruction. Exemplary methods of X-ray computed tomography for measuring changes in absorption and phase shift of the X-ray after passing through the subject include the diffraction enhanced imaging (DEI) method, the X-ray diffraction microscopy and the Talbot method. The method used for the measurement using the X-ray computed tomography in the present embodiment is not particularly limited as long as the information about the tomographic image of $\beta$ and the information about the tomographic image of $\delta$ may be obtained.

Exemplary reconstruction algorithms from the information of sinogram to the information about the tomographic images include the two-dimensional Fourier transformation, the filtered backprojection and the algebraic reconstruction techniques (ART). The method of reconstruction algorithm in the present embodiment is not particularly limited as long as information about the tomographic image may be obtained using the same.

In order to obtain tomographic images of the physical property values, it is necessary to perform radiography, e.g., computed tomography as described above, to obtain tomographic images. In a case in which radiography is performed to obtain transmission images and to obtain transmission images of the physical property values, the method for obtaining physical property values which will be described below may also be applied. In this description, a tomographic image of a physical property value refers to an image which represents distribution of a certain physical property value in a certain cross section. For example, a tomographic image of a complex refractive index refers to an image which represents distribution of the complex refractive index in a certain cross section. Similarly, information about a tomographic image of a certain physical property value refers to information used to construct a tomographic image of a certain physical property value and refers to information which represents distribution of a certain physical property value.

In this description, obtaining the complex refractive index includes not only obtaining the complex refractive index n expressed by Equation (1) but also obtaining $\delta$ and $\beta$.

Next, the step (S102) of obtaining the mass absorption coefficient in accordance with a correlation between the complex refractive index and the mass absorption coefficient will be described.

Figure 5:
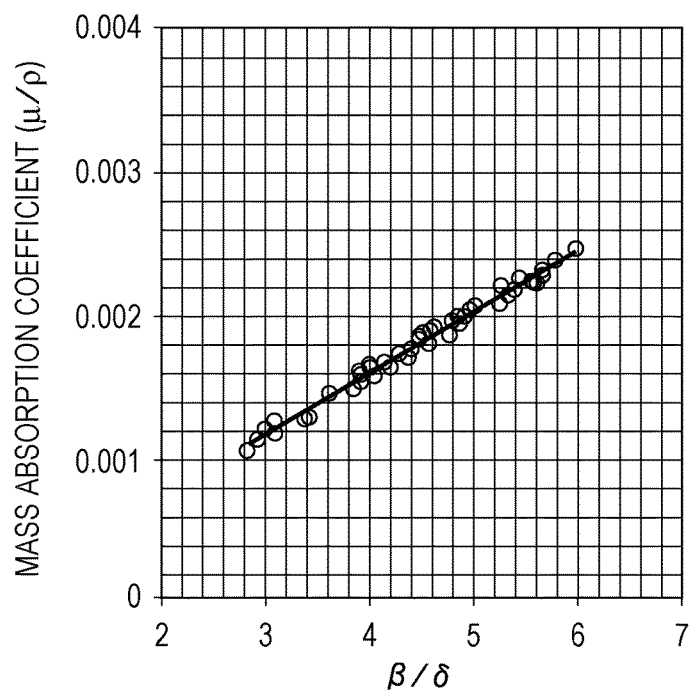
FIG. 5 is a diagram illustrating a relationship between $\beta/\delta$ and mass absorption coefficients $(\mu/\rho)$ in organic compounds including C, H, N and O.

First, the correlation between the complex refractive index and the mass absorption coefficient will be described. FIG. 5 is a graph in which $\delta/\beta$ and the mass absorption coefficients ($\mu/\rho$) regarding a plurality of organic compounds including C, H, N and O are plotted. The X-ray used herein has energy of 9 keV. As illustrated in FIG. 5, the present inventor has found that there is a very strong correlation between the complex refractive index and the mass absorption coefficient. Therefore, it is possible to obtain the mass absorption coefficient in accordance with this correlation. In particular, information about the tomographic image of the mass absorption coefficient of the subject may be obtained by defining the correlation between the complex refractive index and the mass absorption coefficient as a regression curve as expressed by Equation (4) and then substituting, for Equation (4), the information about the tomographic image of $\beta/\delta$ obtained on the basis of $\delta$ and $\beta$ obtained in S101:

[Math. 3]

$$\left(\frac{\mu}{\rho}\right) = f\left(\frac{\beta}{\delta}\right). \tag{4}$$

Obtainment of the information about the tomographic image of the mass absorption coefficient in this step may be performed by calculation using Equation (4) or by any other methods. For example, a table with which a mass absorption coefficient may be obtained on the basis of $\beta/\delta$ may be created previously in accordance with the correlation between the complex refractive index and the mass absorption coefficient as illustrated in FIG. 5, and the mass absorption coefficient of the subject may be obtained by referring to the table.

Next, the step (S103) of obtaining the mass density of the subject using the mass absorption coefficient of the subject will be described.

The information about the tomographic image of the mass density ($\rho$) of the subject may be obtained by dividing the information about the tomographic image of the linear absorption coefficient ($\mu$) by the information about the tomographic image of the mass absorption coefficient ($\mu/\rho$). As is apparent from Equation (3), the information about the tomographic image of the linear absorption coefficient ($\mu$) may be obtained by multiplying the information about the tomographic image of $\beta$ by $4\pi/\lambda$.

Next, the step (S104) of obtaining the average atomic number and the average mass number of the subject using the mass density ($\rho$) of the subject in accordance with the correlation between the average atomic number $<Z>$ and the average mass number $<A>$ will be described.

$\delta$ which is a real part of the complex refractive index may be expressed by the following Equation (5):

[Math. 4]

$$\delta = \frac{\rho N_a r_0 \lambda^2}{2\pi} \frac{\langle Z \rangle}{\langle A \rangle} \tag{5}$$

in which $N_a$ is the Avogadro's number and $r_0$ is the classical electron radius.

Figure 6:
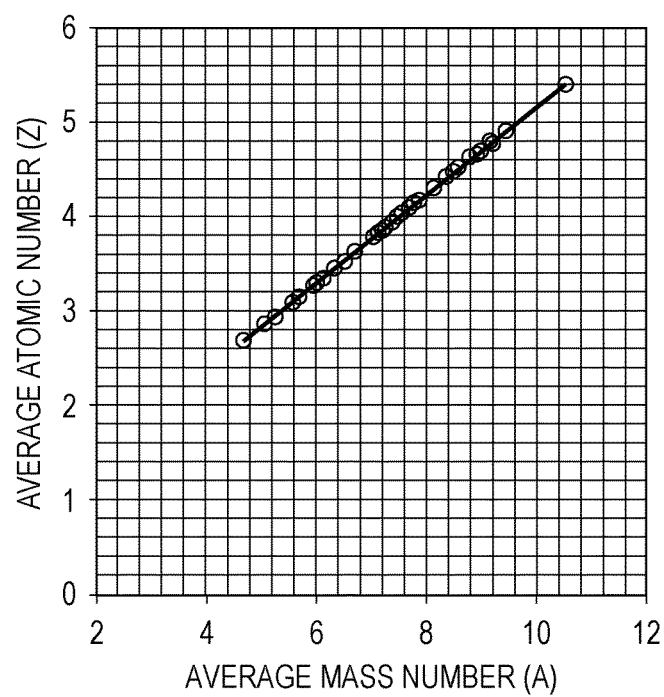
FIG. 6 is a diagram illustrating a relationship between average mass numbers <A> and average atomic numbers <Z> in organic compounds including C, H, N and O.

FIG. 6 is a graph in which average atomic numbers and average mass numbers regarding a plurality of organic compounds including C, H, N and O are obtained and plotted. As illustrated in FIG. 6, the present inventor has found that there is a very strong linear correlation between the average atomic number and the average mass number. The relationship may be formulated as Equation (6):

$$<Z>=a<A>+b \tag{6}$$

in which a and b are constants.

That is, by solving simultaneous equations of Equation (5) and Equation (6), a tomographic image of the average atomic number $<Z>$ and the average mass number $<A>$ may be obtained. If Equation (5) is used, it is possible to obtain the information about the tomographic image of $<Z>/<A>$ without obtaining the average atomic number $<Z>$ and the average mass number $<A>$.

It is also possible to obtain information about a tomographic image of electron density ($\rho_e$) using the information about the tomographic image of $\delta$ obtained in S101.

A relationship between the electron density ($\rho_e$) and $\delta$ is expressed by Equation (7):

[Math. 5]

$$\rho_e = \frac{2\pi}{r_0 \lambda^2} \delta. \tag{7}$$

That is, the information about the tomographic image of the electron density ($\rho_e$) may be obtained by using Equation (7) and the information about the tomographic image of $\delta$ obtained in S101.

With such a computing flow, the mass absorption coefficient, the mass density, the electron density, the average atomic number and the average mass number of the subject may be obtained by using the values of $\delta$ and $\beta$ in the complex refractive index of the X-ray with respect to the subject. In the present embodiment, the method for obtaining all of the mass absorption coefficient, the mass density, the electron density, the average atomic number and the average mass number has been described; however, it is only necessary to obtain the required physical property values. For example, if it is only necessary to obtain the mass density of the subject, only S101 to S103 may be performed. However, components of the subject may be identified easily when various physical property values are obtained.

In the present embodiment, the physical property values of the subject are obtained using the above-described computing flow; however, another computing flow in accordance with the correlation between the complex refractive index and the mass absorption coefficient illustrated in FIG. 5 may also be used. Alternatively, the physical property values of the subject may be obtained without using computation. For example, a table with which the physical property values of the subject may be obtained on the basis of β and δ may be created previously in accordance with the correlation between the complex refractive index and the mass absorption coefficient illustrated in FIG. 5, and the physical property values may be obtained by referring to the table. For example, a table with which the mass density of the subject may be obtained may be created previously on the basis of β and δ and, when the second obtaining unit refers to the table, the mass density of the subject may be obtained without obtaining mass absorption coefficient of the subject. Alternatively, equations and tables with which the physical property values of the subject may be obtained directly from the measurement result of the X-ray measuring device 517 may also be used. In this case, the first obtaining unit and the second obtaining unit are integrated with each other.

EXAMPLE

With reference to FIG. 2, the X-ray measuring system 500 of the present embodiment will be described. The X-ray measuring system 500 includes the X-ray measuring device 517, the computing device 513 which obtains physical property values of the subject 506 in accordance with the measurement result of the X-ray measuring device 517, and a display unit 514 which displays images in accordance with the physical property values obtained by the computing device 513.

The X-ray measuring device 517 includes an X-ray emitter which monochromatizes and shapes the X-ray from an X-ray source 501 and then emits the X-ray toward the subject 506, a movable stage for subject 507, and an X-ray measuring unit which measures an X-ray amount through diffraction of the X-ray which passed through the subject 506.

As the X-ray source 501, a Cu-target rotating anticathode type X-ray source is used. The X-ray emitted from the X-ray source 501 is monochromatized and then shaped by the X-ray emitter.

The X-ray emitter includes an X-ray multi-layer mirror 502, a slit 503, a 4-crystal monochromator 504 and a collimator 505. The X-ray multi-layer mirror 502 monochromatizes and condenses the X-ray emitted from the X-ray source 501. Scattered X-rays from the X-ray multi-layer mirror 502 are shielded by the slit 503. The slit 503 is provided with a rectangular opening which extends 2 mm in the Y direction and 1 mm in the Z direction.

Monochromaticity of the X-ray which has been monochromatized by the X-ray multi-layer mirror 502 is increased by the 4-crystal monochromator 504. At the same time, divergence of the X-ray is controlled by the 4-crystal monochromator 504. The 4-crystal monochromator 504 used herein is Ge single crystal and a diffracting plane used herein is (220). Thus, a characteristic X-ray ($CuK_{\alpha1}$) which is a monochromatized low-divergence X-ray may be used.

The X-ray from the 4-crystal monochromator 504 is shaped into an X-ray having a diameter of 50 micrometers by the collimator 505. The collimator 505 is made of a Pt board having a thickness of 100 micrometers and is provided with an opening having a diameter of 50 micrometers. Note that it is also possible that the collimator 505 is made of a material having high X-ray absorption capability, such as Au, Pb, Ta and W, other than Pt. The X-ray shaped by the collimator 505 is emitted toward the subject 506.

The subject 506 used herein is PET fiber which is 3 mm in diameter. The subject 506 is placed on the stage for subject 507. The stage for subject 507 may be translated in the X, Y and Z directions, and may be rotated around X, Y and Z axes.

The X-ray which has passed through the subject 506 enters the X-ray measuring unit. The X-ray measuring unit includes a slit 508, an analyzer crystal 509, a stage for analyzer crystal 510, a slit 511 and the X-ray detector 512.

The X-ray which has passed through the subject 506 enters the analyzer crystal 509 after passing through the slit 508. The slit 508 used herein is provided with a rectangular opening which extends 1 mm in the Y direction and 1 mm in the Z direction. The analyzer crystal 509 is used to take out the only X-ray that enters at an angle which satisfies diffraction conditions. The analyzer crystal 509 is Ge single crystal and a diffracting plane thereof is (220). The analyzer crystal 509 is provided on the stage for analyzer crystal 510 which rotates about the Y-axis.

The X-ray diffracted by the analyzer crystal 509 passes through the slit 511 and the intensity of the X-ray is measured by the X-ray detector 512. The slit 511 is provided to avoid extra X-ray from the analyzer crystal 509 from entering the X-ray detector 512. The slit 511 is provided with an opening which extends 1 mm in the Z direction and 5 mm in the Y direction. The X-ray detector 512 is a scintillation counter in which NaI crystal is used.

Angular distribution of intensity of the X-ray which enters the analyzer crystal 509 may be measured through measurement of the X-ray intensity regarding particular angle ranges while rotating the analyzer crystal 509 by the stage for analyzer crystal 510 (scan measurement).

Figure 7:
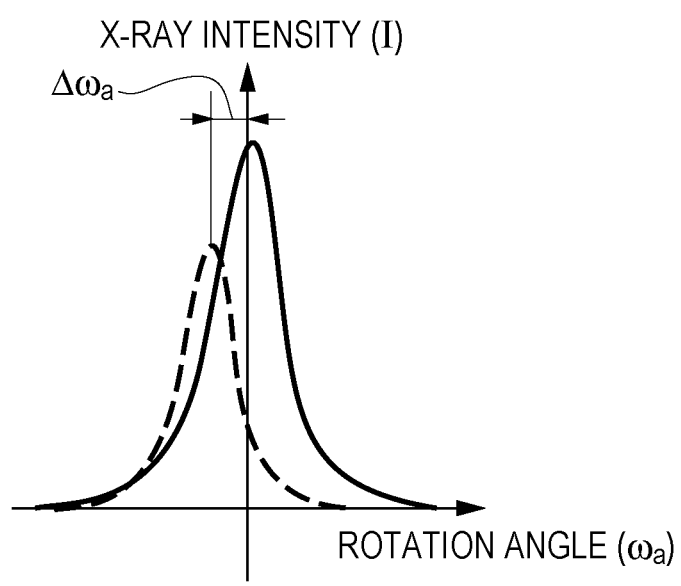
FIG. 7 is a schematic diagram of angular distribution of X-ray intensity.

FIG. 7 is a schematic diagram of the angular distribution of intensity of the X-ray obtained by this measurement. The horizontal axis corresponds to the rotation angle ($\omega_a$) of the analyzer crystal 509 and the vertical axis corresponds to the intensity (I) of the X-ray. The solid line represents the intensity of the X-ray measured with no subject 506 existing while the dotted line represents the intensity of the X-ray which has passed through the subject 506.

Integrated intensity of the X-ray intensity illustrated by the dotted line becomes lower than that of the X-ray intensity illustrated by the solid line due to an effect of absorption by the subject 506 and, in addition to that, since the X-ray is refracted due to the phase shift in the subject 506, the peak itself is shifted by the refraction angle. That is, X-ray transmittance of the subject 506 at the portion illuminated with the X-ray may be obtained on the basis of a rate of change between the integrated intensity of the dotted line and the integrated intensity of the solid line. Further, the refraction angle of the portion illuminated with the X-ray may be obtained on the basis of a peak shift amount ($\Delta\omega_a$).

By moving the stage for subject 507, the subject 506 is moved in the Z direction by 50 micrometers each time and a scan measurement is carried out by the analyzer crystal 509 at each point.

Then the subject 506 is rotated by one degree each time about the Y-axis (θ rotation) and the same measurement is carried out at each angle. The measurement range of θ is 1 to 180 degrees. These measurement results are transmitted to the computing device 513. The computing device 513 obtains the X-ray transmittance and the refraction angle of the subject 506 on the basis of the measurement results, and also obtains the information about the tomographic image of the complex refractive index. Then, as described above, the physical property values of the subject are obtained in accordance with the correlation between the complex refractive index and the mass absorption coefficient.

The computing flow to be performed by the computing device 513 will be described in detail. First, the exemplary step (S101) of obtaining the complex refractive index on the basis of the measurement result of the X-ray measuring device 517 will be described. This step is performed by the first obtaining unit.

The integrated intensity of the X-ray at each θ is obtained on the basis of the measurement result and the obtained integrated intensity is divided by the integrated intensity of the X-ray measured with no subject 506 existing to obtain transmittance T(θ,Z). μt(θ,Z) at each portion of the subject 506 is obtained using the following Equation (8) on the basis of transmittance T:

$$\mu t(\theta, Z) = -\ln(T(\theta, Z)) \quad (8).$$

Then, differential phase values are obtained using the following Equation (9) on the basis of the refraction angle $\Delta\omega_a(\theta, Z)$ at each θ:

[Math. 6]

$$\frac{d\phi(\theta, Z)}{dz} = \frac{2\pi}{\lambda} \Delta\omega_a(\theta, Z). \quad (9)$$

By integrating these differential phase values in the Z direction, a phase shift amount $\phi(\theta, Z)$ in the subject 506 is obtained.

The tomographic image is reconstructed using the ART algorithm on the basis of μt(θ,Z) and φ(θ,Z) with θ being from 1 to 180 degrees, and the information about the tomographic image is obtained. The tomographic image of β is obtained using Equation (3) on the basis of the tomographic image obtained from μt(θ,Z), and then the tomographic image of δ is obtained using Equation (2) on the basis of the tomographic image obtained from φ(θ,Z).

Next, the exemplary step (S102) of obtaining the information about the tomographic image of the mass absorption coefficient of the subject in accordance with the correlation between the complex refractive index and the mass absorption coefficient will be described. This step is performed by the second obtaining unit. The information about the tomographic image of β/δ is obtained on the basis of the information about the complex refractive index obtained in S101, and the information about the tomographic image of the mass absorption coefficient (μ/ρ) is obtained by using a relationship between β/δ and the mass absorption coefficient (μ/ρ) previously fit linearly as a regression curve.

Next, the exemplary step (S103) of obtaining the information about the tomographic image of the mass density of the subject using the mass absorption coefficient will be described. Information about the tomographic image of μ is obtained on the basis of μt(θ,Z) obtained in S101. Then the information about the tomographic image of the mass density ρ is obtained by dividing the information about the tomographic image of μ by the information about the tomographic image of the mass absorption coefficient.

Next, the exemplary step (S104) of obtaining the average atomic number <Z> and the average mass number <A> of the subject using the mass density in accordance with the correlation between the average atomic number and the average mass number will be described. First, information about the tomographic image of <Z>/<A> is obtained on the basis of information about ρ tomographic images and information about δ tomographic images. Then, information about the tomographic image of the average atomic number <Z> and the average mass number <A> of the subject 506 is obtained using the regression curve of the average atomic number <Z> and the average mass number <A>.

Information about the tomographic image of the electron density ($\rho_e$) is obtained on the basis of the information about the tomographic image of δ using Equation (7)

The tomographic images of the mass absorption coefficient, the mass density, the electron density, the average atomic number and the average mass number of the subject computed by the computing device 513 may also be displayed on the display unit 514. As the display unit 514, a PC monitor may be used, for example.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-248625, filed Nov. 12, 2012, which is hereby incorporated by reference herein in its entirety.

REFERENCE SIGNS LIST

512 X-ray detector
513 computing device
514 display unit

The invention claimed is:

1. A computing device configured to obtain information about a subject using a detection result detected by an X-ray detector which detects a monochromatic X-ray transmitted through the subject irradiated with a monochromatic X-ray in a certain wavelength, the device comprising:
   a unit configured to obtain detection results detected by the X-ray detector;
   a first obtaining unit configured to obtain information about a tomographic image of a complex refractive index n of the subject for the monochromatic X-ray; and
   a second obtaining unit configured to obtain information about a tomographic image of a mass absorption coefficient (μ/ρ) of the subject in accordance with a correlation between a parametric ratio (β/δ) according to a complex refractive index n and the mass absorption coefficient (μ/ρ), where μ denotes a linear absorption coefficient of a subject for a monochromatic X-ray in a certain wavelength, ρ denotes mass density, n denotes a complex refractive index of a subject for a monochromatic X-ray in a certain wavelength, and 1−δ and −β respectively denote a real part and an imaginary part in the complex refractive index n, wherein the detection results are detected at different angles while changing an irradiation angle of the monochromatic X-ray with respect to the subject.

2. The computing device according to claim 1, wherein the second obtaining unit uses the following Equation as the correlation between the parametric ratio (β/δ) according to the complex refractive index n and the mass absorption coefficient (μ/ρ):

[Math. 1]

$$\left(\frac{\mu}{\rho}\right) = f\left(\frac{\beta}{\delta}\right)$$

$$n = 1 - \delta - i\beta.$$

3. The computing device according to claim 1, wherein the information about the subject is at least any one of mass density, an average atomic number and an average mass number of the subject.

4. The computing device according to claim 1, wherein the second obtaining unit obtains the mass absorption coefficient on the basis of the complex refractive index, and obtains information about the subject on the basis of the mass absorption coefficient.

5. The computing device according to claim 3, wherein the second obtaining unit obtains any one value of the average atomic number and the average mass number of the subject using the other value of the average atomic number and the average mass number of the subject and a linear correlation between an average atomic numbers and an average mass numbers.

6. The computing device according to claim 1, wherein the second obtaining unit obtains the information about the subject using a complex refractive index of the subject for a monochromatic X-ray.

7. The computing device according to claim 1, wherein the second obtaining unit obtains the mass absorption coefficient and the mass absorption coefficient is obtained using a regression curve of β/δ and the mass absorption coefficient, δ and β being expressed by following formula:

$$n = 1 - \delta - i\beta$$

in which n is a complex refractive index of the subject for an X-ray.

8. The computing device according to claim 1, wherein:
the first obtaining unit obtains a distribution of the complex refractive index n of the subject for an X-ray after passing through the subject; and
the second obtaining unit obtains a distribution of information about the subject.

9. An X-ray measuring system, comprising:
the computing device according to claim 1; and
an X-ray detector configured to detect an X-ray transmitted through a subject irradiated with a monochromatic X-ray in a certain wavelength, wherein the computing device is configured to obtain information about the subject using the detection result detected by the X-ray detector.

10. A non-transitory computer-readable storage medium storing, in executable form, a program configured to let a computing device execute the following:
obtaining information about a tomographic image of a complex refractive index of a subject for a monochromatic X-ray using detection results of the monochromatic X-ray transmitted through the subject; and
obtaining information about a tomographic image of a mass absorption coefficient (μ/ρ) of the subject in accordance with a correlation between a parametric ratio (β/δ) according to a complex refractive index n and the a mass absorption coefficient (μ/ρ),
where μ denotes a linear absorption coefficient of a subject for a monochromatic X-ray in a certain wavelength, ρ denotes mass density, n denotes a complex refractive index of a subject for a monochromatic X-ray in a certain wavelength, and 1−δ and −β respectively denote a real part and an imaginary part in the complex refractive index n,
wherein the detection results are measured at different angles while changing an irradiation angle of the monochromatic X-ray with respect to the subject.

11. A measuring method for obtaining information about a subject using a monochromatic X-ray, comprising:
irradiating the subject with the monochromatic X-ray in a certain wavelength;
detecting the X-ray transmitted through the subject;
obtaining information about a tomographic image of a complex refractive index of the subject for the monochromatic X-ray using a detection result in the detecting step; and
obtaining information about a tomographic image of a mass absorption coefficient (μ/ρ) of the subject in accordance with a correlation between a parametric ratio (β/δ) according to a the complex refractive index n and a mass absorption coefficient (μ/ρ),
where μ denotes a linear absorption coefficient of a subject for a monochromatic X-ray in a certain wavelength, ρ denotes mass density, n denotes a complex refractive index of a subject for a monochromatic X-ray in a certain wavelength, and 1−δ and −β respectively denote a real part and an imaginary part in the complex refractive index n,
wherein the detection results are measured at different angles while changing an irradiation angle of the monochromatic X-ray with respect to the subject.

12. A computing device configured to obtain information about a subject using a detection result detected by an X-ray detector which detects a monochromatic X-ray transmitted through the subject irradiated with a monochromatic X-ray in a certain wavelength, the device comprising:
a unit configured to obtain detection results detected by the X-ray detector;
a first obtaining unit configured to obtain information about a tomographic image of a complex refractive index n of the subject for the monochromatic X-ray; and
a second obtaining unit configured to obtain information about a tomographic image of a mass absorption coefficient (μ/ρ) of the subject in accordance with a correlation between a parametric ratio (β/δ) according to a complex refractive index n and the mass absorption coefficient (μ/ρ), where μ denotes a linear absorption coefficient of a subject for a monochromatic X-ray in a certain wavelength, ρ denotes mass density, n denotes a complex refractive index of a subject for a monochromatic X-ray in a certain wavelength, and 1−δ and −β respectively denote a real part and an imaginary part in the complex refractive index n.

13. The computing device according to claim 12, wherein the second obtaining unit uses the following Equation as the correlation between the parametric ratio (β/δ) according to the complex refractive index n and the mass absorption coefficient (μ/ρ):

$$\left(\frac{\mu}{\rho}\right) = f\left(\frac{\beta}{\delta}\right)$$ [Math. 1]

$$n = 1 - \delta - i\beta.$$

14. The computing device according to claim 12, wherein the information about the subject is at least any one of mass density, an average atomic number and an average mass number of the subject.

15. The computing device according to claim 12, wherein the second obtaining unit obtains the mass absorption coefficient on the basis of the complex refractive index, and obtains information about the subject on the basis of the mass absorption coefficient.

16. The computing device according to claim 14, wherein the second obtaining unit obtains any one value of the average atomic number and the average mass number of the subject using the other value of the average atomic number and the average mass number of the subject and a linear correlation between an average atomic numbers and an average mass numbers.

17. The computing device according to claim 12, wherein the second obtaining unit obtains the information about the subject using a complex refractive index of the subject for a monochromatic X-ray.

18. The computing device according to claim 12, wherein the second obtaining unit obtains the mass absorption coefficient and the mass absorption coefficient is obtained using a regression curve of β/δ and the mass absorption coefficient, δ and β being expressed by following formula:

$$n = 1 - \delta - i\beta$$

in which n is a complex refractive index of the subject for an X-ray.

19. The computing device according to claim 12, wherein:
the first obtaining unit obtains a distribution of the complex refractive index n of the subject for an X-ray after passing through the subject; and
the second obtaining unit obtains a distribution of information about the subject.

20. The computing device according to claim 12, wherein:
a tomographic image of the linear absorption coefficient μ is obtained based on the tomographic image of the imaginary part β in the complex refractive index n obtained by the first obtaining unit.

21. The computing device according to claim 20, wherein:
a tomographic image of the mass density ρ is obtained by the tomographic image of the mass absorption coefficient (μ/ρ) obtained by the second obtaining unit and the tomographic image of the linear absorption coefficient μ.

22. An X-ray measuring system, comprising:
the computing device according to claim 12; and
an X-ray detector configured to detect an X-ray transmitted through a subject irradiated with a monochromatic X-ray in a certain wavelength,
wherein the computing device is configured to obtain information about the subject using the detection result detected by the X-ray detector.

23. A non-transitory computer-readable storage medium storing, in executable form, a program configured to let a computing device execute the following:
obtaining information about a tomographic image of a complex refractive index of a subject for a monochromatic X-ray using detection results of the monochromatic X-ray transmitted through the subject; and
obtaining information about a tomographic image of a mass absorption coefficient (μ/ρ) of the subject in accordance with a correlation between a parametric ratio (β/δ) according to a complex refractive index n and the mass absorption coefficient (μ/ρ),
where μ denotes a linear absorption coefficient of a subject for a monochromatic X-ray in a certain wavelength, ρ denotes mass density, n denotes a complex refractive index of a subject for a monochromatic X-ray in a certain wavelength, and 1−δ and −β respectively denote a real part and an imaginary part in the complex refractive index n.

24. A measuring method for obtaining information about a subject using a monochromatic X-ray, comprising:
irradiating the subject with the monochromatic X-ray in a certain wavelength;
detecting the X-ray transmitted through the subject;
obtaining information about a tomographic image of a complex refractive index of the subject for the monochromatic X-ray using detection results in the detecting step; and
obtaining information about a tomographic image of a mass absorption coefficient (μ/ρ) of the subject in accordance with a correlation between a parametric ratio (β/δ) according to a complex refractive index n and a mass absorption coefficient (μ/ρ),
where μ denotes a linear absorption coefficient of a subject for a monochromatic X-ray in a certain wavelength, ρ denotes mass density, n denotes a complex refractive index of a subject for a monochromatic X-ray in a certain wavelength, and 1−δ and −β respectively denote a real part and an imaginary part in the complex refractive index n.

* * * * *